US 6,350,914 B1

(12) United States Patent  
Eller et al.

(10) Patent No.: US 6,350,914 B1
(45) Date of Patent: Feb. 26, 2002

(54) PREPARATION OF AMINES FROM OLEFINS OVER ZEOLITES HAVING AN NES STRUCTURE

(75) Inventors: Karsten Eller, Ludwigshafen; Rudolf Kummer, Frankenthal; Matthias Dernbach, Eppelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/897,683

(22) Filed: Jul. 21, 1997

(30) Foreign Application Priority Data

Jul. 30, 1996 (DE) ......................... 196 30 670

(51) Int. Cl.⁷ .......................................... C07C 209/60
(52) U.S. Cl. ..................................... 564/485
(58) Field of Search ......................... 564/485

(56) References Cited

U.S. PATENT DOCUMENTS

| 4,375,002 A | 2/1983 | Peterson et al. | 564/445 |
| 4,536,602 A | 8/1985 | Deeba | 564/485 |
| 4,929,758 A | 5/1990 | Taglieber et al. | 564/485 |
| 5,254,514 A | 10/1993 | Nakagawa | 502/62 |
| 5,641,393 A | 6/1997 | Nakagawa | 208/46 |
| 5,739,405 A | 4/1998 | Eller et al. | 564/485 |

FOREIGN PATENT DOCUMENTS

| CA | 2092964 | 6/1994 |
| DE | 4206992 | 3/1992 |
| EP | 101 921 | 3/1984 |
| EP | 132 736 | 7/1984 |
| EP | 133 938 | 7/1984 |
| EP | 305 564 | 3/1989 |
| EP | 378916 | 7/1990 |
| EP | 431 451 | 11/1990 |
| EP | 587424 | 3/1994 |
| EP | 778259 | 6/1997 |

OTHER PUBLICATIONS

Brunet et al., *J. Mol. Catal.*, 49, 1989, pp. 235–259.
Meier et al., *Atlas of Zeolite Structure Types*, 3rd. Ed., 1992, pp. 154–155.
Shannon et al., *Nature*, 353, 1991, pp. 417–420.
Nakagawa, *Stud. Surf. Sci. Catal.*, 84, 1994, pp. 323–330.
Corma et al., *Stud. Surf. Sci. Catal.*, 37, 1987, pp. 495–503.

*Primary Examiner*—Samuel Barts
(74) *Attorney, Agent, or Firm*—Keil & Weinkauf

(57) ABSTRACT

In a process for preparing amines of the general formula I

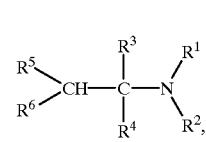

(I)

where $R_1, R^2, R^3, R^4, R^5, R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkyl-cycloalkyl, $C_4$–$C_{20}$-cycloalkyl-alkyl, aryl, $C_7$–$C_{20}$-alkylaryl or $C_7$–$C_{20}$-aralkyl, $R^1$ and $R^2$ are together a saturated or unsaturated divalent $C_3$–$C_9$-alkylene chain and $R^3$ or $R^5$ are $C_{21}$–$C_{200}$-alkyl, $C_{21}$–$C_{200}$-alkenyl or together a divalent $C_2$–$C_{12}$-alkylene chain, by reacting olefins of the general formula II

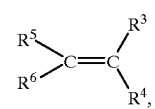

(II)

where $R^3$, $R^4$, $R^5$ and $R^6$ are as defined above, with ammonia or primary or secondary amines of the general formula III

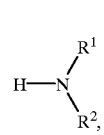

(III)

where $R^1$ and $R^2$ are as defined above, at from 200 to 350° C. and pressures of from 100 to 300 bar in the presence of a heterogeneous catalyst, the heterogeneous catalyst used is a zeolite having an NES structure.

12 Claims, No Drawings

PREPARATION OF AMINES FROM OLEFINS OVER ZEOLITES HAVING AN NES STRUCTURE

The present invention relates to a process for preparing amines by reacting ammonia or primary or secondary amines with olefins at elevated temperatures and pressures in the presence of zeolites having an NES structure.

An overview of the methods for aminating olefins is given in "Functionalisation of Alkenes: Catalytic Amination of Monoolefins", J. J. Brunet et al. J.Mol.Catal., 49 (1989), pages 235 to 259.

There are fundamentally two catalysis mechanisms. The olefin is coordinated to form a metal complex. This activated species can be attacked by the nucleophilic amine and form a higher aminated product. The amine can be chemisorbed on acid centers or metal centers (via metal amides) and be reacted in this activated form with the olefin.

Zeolites are very useful catalysts. They have a high number of catalytically active centers combined with a large surface area. The zeolites described differ in type and in the after-treatment (eg. thermal treatment, dealumination, acid treatment, metal ion exchange, etc.). Examples may be, found in U.S. Pat. Nos. 4,375,002, 4,536,602, EP-A-305 564, EP-A-101 921, DE-A-42 06 992.

EP-A-133 938, EP-A-431 451 and EP-A-132 736 disclose processes in which borosilicate, gallium silicate, aluminosilicate and iron silicate zeolites are used for the preparation of amines from olefins and refer to the possibility of doping these zeolites with alkali, alkaline earth and transition metals.

CA-A-2 092 964 discloses a process for preparing amines from olefins in which BETA-zeolites, which are defined as crystalline aluminosilicates having a particular composition and a pore size of more than 5 Å, are used. Preference is given to using metal- or halogen-modified Beta-zeolites.

All processes for synthesizing amines from olefins over these catalysts give a low amine yield or a low space-time yield, or lead to rapid deactivation of the catalysts.

It is an object of the present invention to remedy these disadvantages.

We have found that this object is achieved by a new and improved process for preparing amines of the general formula I

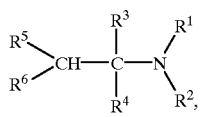
(I)

where $R^1, R^2, R^3, R^4, R^5, R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkyl-cycloalkyl, $C_4$–$C_{20}$-cycloalkyl-alkyl, aryl, $C_7$–$C_{20}$-alkylaryl or $C_7$–$C_{20}$-aralkyl, $R^1$ and $R^2$ are together a saturated or unsaturated divalent $C_3$–$C_9$-alkylene chain and $R^3$ or $R^5$ are $C_{21}$–$C_{200}$-alkyl, $C_{21}$–$C_{200}$-alkenyl or together a divalent $C_2$–$C_{12}$-alkylene chain, by reacting olefins of the general formula II

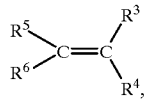
(II)

where $R^3$, $R^4$, $R^5$ and $R^6$ are as defined above, with ammonia or primary or secondary amines of the general formula III

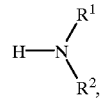
(III)

where $R^1$ and $R^2$ are as defined above, at from 200 to 350° C. and pressures of from 100 to 300 bar in the presence of a heterogeneous catalyst, wherein the heterogeneous catalyst used is a zeolite having an NES structure.

The process of the present invention can be carried out as follows:

The olefin II and ammonia or the primary or secondary amine III can be reacted at from 200 to 350° C., preferably from 220 to 330° C., particularly preferably from 230 to 320° C., and pressures of from 100 to 300 bar, preferably from 120 to 300 bar, particularly preferably from 140 to 290 bar, in the presence of zeolites having an NES structure as catalyst, eg. in a pressure reactor, and, preferably, the amine obtained is separated off and the unreacted starting materials are recirculated.

The present invention gives a very good yield at high selectivity and at a high space-time yield. In addition, the deactivation of the catalyst has been suppressed.

In the process of the present invention, even with a low excess of ammonia or amine, a high selectivity to the desired reaction product is achieved and the dimerization and/or oligomerization of the olefin used is avoided.

One embodiment of this process comprises feeding a mixture of ammonia and/or amines III with the olefin II in a molar ratio of 1:1 to 5:1 to a fixed-bed reactor and reacting this mixture at from 200 to 350° C. and a pressure of from 100 to 300 bar in the gas phase or in the supercritical state.

The desired product can be obtained from the mixture leaving the reactor by means of known methods, for example distillation or extraction, and can, if necessary, be brought to the desired purity by means of further separation operations. In general, the unreacted starting materials are preferably recirculated to the reactor.

It is possible to use monounsaturated or polyunsaturated olefins II, in particular those having from 2 to 10 carbon atoms or mixtures thereof, and polyolefins as starting materials. Owing to their less pronounced polymerization tendency, monoolefins are more suitable than diolefins and polyolefins, although the latter can be reacted equally selectively by means of higher excesses of ammonia or amine. The position of the equilibrium and thus the conversion to the desired amine is very strongly dependent on the reaction pressure selected. High pressure favors the addition product, although the pressure range up to 300 bar generally represents the optimum for technical and economic reasons. The selectivity of the reaction is influenced to a great extent by the temperature, as well as by parameters such as ammonia/amine excess and catalyst. Although the reaction rate of the addition reaction increases greatly with rising temperature, competing cracking and recombination reactions of the olefin are promoted at the same time. In addition, a temperature increase is not advantageous from a thermodynamic point of view. The position of the temperature optimum in respect of conversion and selectivity is dependent on the constitution of the olefin, the amine used and the catalyst and is usually in the range from 200 to 350° C.

Suitable catalysts for the amination of olefins are zeolites having an NES structure, preferably NU-87 zeolites, which are known, for example, from EP-A-377 291.

Zeolites having an NES structure have a two-dimensional pore system with the approximate dimensions 4.7×6.0 Å (Meier, Olson, Atlas of Zeolite Structure Types, 3rd Ed., 1992, Butterworth-Heinemann, pages 154 to 155). An example of a zeolite having an NES structure is NU-87 (Shannon et al., Nature 353 (1991), pp. 417 to 420). The structure of SSZ-37 (U.S. Pat. No. 5,254,514) has not yet been finally established, but it appears to be related to NU-87 (Nakagawa, Stud. Surf. Sci. Catal. 84 (1994), pages 323 to 330), so that for the purposes of this application it should also be included among the zeolites having an NES structure of the present invention.

Apart from the NES zeolites containing aluminum as trivalent element in the $SiO_2$ matrix, as is the case, for example, in NU-87, for the purposes of this application other elements are also possible if acid centers are created by their incorporation. This is the case, for example, for borozeolites, iron zeolites or gallium zeolites. The molar ratio of $SiO_2$ to the oxides of the trivalent elements are known as the modulus $SiO_2/M_2O_3$ (M=Al, B, Ga, Fe), can vary from virtually infinity to a few tens depending on the class of zeolite.

Apart from the classical zeolites based on $SiO_2$, it is also possible to obtain analogous structures based on aluminum phosphates, known as AlPOs. If these contain aluminum and phosphorus in a ratio of greater than 1, they are likewise acid and can be used for the purposes of the present invention. If part of the phosphorus and/or both aluminum and phosphorus is replaced by silicon, this gives the SAPOs which are likewise acid. If various metal ions such as Li, B, Be, Mg, Ti, Mn, Fe, Co, Zn, Ga, Ge, As are present in addition to aluminum and phosphorus, the compounds are referred to as MeAPOs, or in the simultaneous presence of silicon as MeAPSOs, in which the negative charge of the $Me_aAl_bP_c$-$Si_dO_e$ framework is in each case balanced by cations. All such molecular sieves having an NES structure are included among the catalysts of the present invention.

The zeolites having an NES structure of the present invention can be shaped as such or else together with a binder in a weight ratio of from 98:2 to 40:60 to give extrudates or pellets. Suitable binders are various aluminum oxides, preferably boehmite, amorphous aluminosilicates having an $SiO_2/Al_2O_3$ ratio of from 25:75 to 95:5, silicon dioxide, preferably finely divided $SiO_2$, mixtures of finely divided $SiO_2$ and finely divided $Al_2O_3$, finely divided $TiO_2$ and also clays. After shaping, the extrudates or compacts are advantageously dried at 110° C. for 16 hours and calcined at from 200 to 500° C. for from 2 to 16 hours, with the calcination also being able to be carried out directly in the amination reactor.

To increase the selectivity, the operating load and the number of possible regenerations, various modifications can be made to the zeolite catalysts having an NES structure of the present invention.

One modification of the catalysts comprises ion-exchanging or doping the unshaped or shaped zeolites with alkali metals such as Na and K, alkaline earth metals such as Ca and Mg, earth metals such as Tl, transition metals such as Ti, Zr, Mn, Fe, Mo, Cu, Zn and Cr, noble metals and/or rare earth metals such as La, Ce or Y.

In an advantageous embodiment, the shaped zeolites having an NES structure of the present invention are placed in a flow tube and, for example, a halide, an acetate, an oxalate, a citrate or a nitrate of the abovedescribed metals in dissolved form is passed over them at from 20 to 100° C. Such an ion exchange can, for example, be carried out on the hydrogen, ammonium or alkali metal form of the zeolites having an NES structure of the present invention.

A further possible way of applying the metal to the zeolites having an NES structure of the present invention comprises impregnating the material, for example, with a halide, an acetate, an oxalate, a citrate, a nitrate or an oxide of the abovedescribed metals in aqueous or alcoholic solution.

Both ion exchange and impregnation can be followed by drying and if desired repeated calcination. In the case of metal-doped zeolites having an NES structure, an after-treatment with hydrogen and/or with steam can be useful.

A further possible way of modifying the zeolites comprises subjecting the zeolites having an NES structure of the present invention, shaped or unshaped, to a treatment with acids such as hydrochloric acid (HCl), hydrofluoric acid (HF), sulfuric acid ($H_2SO_4$), phosphoric acid ($H_3PO_4$), oxalic acid ($HO_2C—CO_2H$) or mixtures thereof.

In a particular embodiment, the zeolites having an NES structure of the present invention are treated prior to shaping with one of the acids mentioned in a concentration of from 0.001 N to 2 N, preferably from 0.05 to 0.5 N, for from 1 to 100 hours under reflux. After being filtered off and washed, they are generally dried at from 100 to 160° C. and calcined at from 200 to 600° C. A further particular embodiment comprises an acid treatment of the zeolites having an NES structure of the present invention after they have been shaped with binders. Here, the zeolite of the present invention is generally treated for from 1 to 3 hours at from 60 to 80° C. with a 3–25% strength acid, in particular a 12–20% strength acid, subsequently washed, dried at from 100 to 160° C. and calcined at from 200 to 600° C. Here too, the calcination can again be carried out directly in the amination reactor.

A further possible way of modifying the zeolites is given by an exchange with ammonium salts, eg. $NH_4Cl$, or with monoamines, diamines or polyamines. Here, the zeolite shaped together with binder is generally exchanged continuously at from 60 to 80° C. with 10–25% strength, preferably 20% strength, $NH_4Cl$ solution for 2 hours in a weight ratio of zeolite/ammonium chloride solution of 1:15 and then dried at from 100 to 120° C.

A further modification which can be made to the zeolites of the present invention is dealumination in the case of aluminum zeolites, where a part of the aluminum atoms is replaced by silicon or the zeolites have their aluminum content depleted by, for example, hydrothermal treatment. A hydrothermal dealumination is advantageously followed by extraction with acids or complexing agents in order to remove non-lattice aluminum formed. The replacement of aluminum by silicon can, for example, be carried out by means of $(NH_4)_2SiF_6$ or $SiCl_4$. Examples of dealuminations of Y-zeolites may be found in Corma et al., Stud. Surf. Sci. Catal. 37 (1987), pages 495 to 503. In the case of other trivalent oxides, the modulus can be increased similarly by a part of the boron, the iron or the gallium being leached out or replaced by silicon.

The catalysts can be used as extrudates having diameters of, for example, from 1 to 4 mm or as pellets having diameters of, for example, from 3 to 5 mm for the amination of the olefins.

A fluidizable material having a particle size of from 0.1 to 0.8 mm can be obtained from the shaped catalyst, for example in the form of extrudates, by milling and sieving.

The substituents $R^1$, $R^2$, $R^3$, $R^4$, $R^5$ and $R^6$ in the compounds I, II and III have the following meanings:

$R^1$, $R^2$, $R^3$, $R^4$, $R^5$, $R^6$
- hydrogen,
- $C_1$–$C_{20}$-alkyl, preferably $C_1$–$C_{12}$-alkyl, particularly preferably $C_1$–$C_8$-alkyl such as methyl, ethyl, n-propyl, iso-propyl, n-butyl, iso-butyl, sec-butyl, tert-butyl, n-pentyl, iso-pentyl, n-hexyl, iso-hexyl, n-heptyl, iso-heptyl, n-octyl and iso-octyl,
- $C_2$–$C_{20}$-alkenyl, preferably $C_2$–$C_{12}$-alkenyl, particularly preferably $C_2$–$C_8$-alkenyl such as vinyl and allyl,
- $C_2$–$C_{20}$-alkynyl, preferably $C_2$–$C_8$-alkynyl, in particular $C_2H$ and propargyl,
- $C_3$–$C_{20}$-cycloalkyl, preferably $C_3$–$C_{12}$-cycloalkyl, particularly preferably $C_5$–$C_8$-cycloalkyl such as cyclopentyl, cyclohexyl, cycloheptyl and cyclooctyl,
- $C_4$–$C_{20}$-alkyl-cycloalkyl, preferably $C_4$–$C_{12}$-alkyl-cycloalkyl, particularly preferably $C_5$–$C_{10}$-alkyl-cycloalkyl,
- $C_4$–$C_{20}$-cycloalkyl-alkyl, preferably $C_4$–$C_{12}$-cycloalkyl-alkyl, particularly preferably $C_5$–$C_{10}$-cycloalkyl-alkyl,
- aryl such as phenyl, 1-naphthyl and 2-naphthyl, preferably phenyl,
- $C_7$–$C_{20}$-alkylaryl, preferably $C_7$–$C_{16}$-alkylaryl, particularly preferably $C_7$–$C_{12}$-alkylphenyl such as 2-methylphenyl, 3-methylphenyl, 4-methylphenyl, 2-ethylphenyl, 3-ethylphenyl and 4-ethylphenyl,
- $C_7$–$C_{20}$-aralkyl, preferably $C_7$–$C_{16}$-aralkyl, particularly preferably $C_7$–$C_{12}$-phenalkyl such as phenylmethyl, 1-phenylethyl and 2-phenylethyl, $R^1$ and $R^2$
- together a saturated or unsaturated divalent $C_3$–$C_9$-alkylene chain, preferably —$(CH_2)_4$—, —$(CH_2)_5$—, —$(CH_2)_7$— and —CH=CH—CH=CH—, $R^3$ or $R^5$
- $C_{21}$–$C_{200}$-alkyl, preferably $C_{40}$–$C_{200}$-alkyl such as polybutyl, polyisobutyl, polypropyl, polyisopropyl and polyethyl, particularly preferably polybutyl and polyisobutyl,
- $C_{21}$–$C_{200}$-alkenyl, preferably $C_{40}$–$C_{200}$-alkenyl, particularly preferably $C_{70}$–$C_{170}$-alkenyl, $R^3$ and $R^5$
- together a divalent $C_2$–$C_{12}$-alkylene chain, preferably a divalent $C_3$–$C_8$-alkylene chain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst Syntheses

Catalyst A: Na-NU-87

Solution A was made up from 11.4 g of NaOH and 6.6 g of sodium aluminate in 360 g of water. Solution B was made up from 56.4 g of decamethonium bromide in 360 g of water. Solution C was made up from 165 g of Ludox© AS 40 in 55.2 g of water. Solution A was added to solution C while stirring, stirred further for 5 minutes and solution B was then added. A further 255 g of water were added and the mixture was stirred for a further 30 minutes. The mixture was then transfered to an autoclave and crystallized while stirring for 400 hours at 180° C. under the autogenous pressure. The zeolite formed was filtered off and washed, dried for 4 hours at 110° C. and calcined for 16 hours at 500° C. It had a modulus of 30.

Catalyst B: H-NU-87

50 g of catalyst A were stirred with 750 g of a 20% strength $NH_4Cl$ solution for 2 hours at 80° C. and subsequently filtered off and washed with 2 l of water. After again being exchanged with $NH_4Cl$ and washed again, the zeolite was dried for 2 hours at 120° C. and calcined for 5 hours at 500° C. The entire procedure was then repeated once more.

45 g of the exchanged zeolite were compacted together with 30 g of boehmite and 1.5 g of formic acid in a kneader and kneaded for 40 minutes with addition of water (50 ml). 2 mm extrudates were produced on a ram extruder using a pressure of 50 bar and these were dried for 16 hours at 120° C. and calcined for 16 hours at 500° C. They had a residual sodium content of 0.13% and a BET surface area of 402 $m^2g^{-1}$.

Catalyst C: H-NU-87

20 g of catalyst B were ion-exchanged with 20% strength $NH_4NO_3$ solution for 6 hours at 80° C. in a flow tube. After washing with 10 l of water, the catalyst was dried for 4 hours at 120° C. and calcined for 5 hours at 500° C. The extrudates still contained 0.05% of Na after calcination.

Catalyst D: Na-NU-87

Catalyst D was prepared using a method similar to catalyst A, but was crystallized for only 300 hours.

Catalyst E: H-NU-87

Catalyst E was ion-exchanged using a method similar to catalyst B, but was prepared from catalyst D. The residual sodium content was less than 0.01%. 45 g of the exchanged zeolite were compacted together with 30 g of boehmite and 1.5 g of formic acid in a kneader and kneaded for 35 minutes with addition of water (64 ml). 2 mm extrudates were produced in a ram extruder using a pressure of 55 bar and these were dried for 4 hours at 120° C. and calcined for 16 hours at 500° C.

AMINATION EXAMPLES

The experiments were carried out in a tube reactor (6 mm internal diameter) under isothermal conditions at from 260° C. to 300° C. and a pressure of 280 bar using a mixture of isobutene and ammonia in a molar ratio of 1:1.5. The reaction products were analyzed by gas chromatography.

The results are shown in Table 1.

TABLE 1 tert-Butylamine ($NH_3$: $C_4H_8$ = 1.5)

tert-Butylamine yield [% by weight]

| Cat. | Temperature [° C.] | WHSV 0.38 [g/g·h] | WHSV 0.75 [g/g·h] | WHSV 1.5 [g/g·h] | WHSV 3 [g/g·h] | Density [kg/l] |
|---|---|---|---|---|---|---|
| B | 260 | 25.10 | 22.56 | 19.36 | 14.43 | 0.56 |
| B | 270 | | 21.91 | 20.11 | 17.94 | 0.56 |
| B | 280 | | 18.06 | 17.69 | 17.13 | 0.56 |

TABLE 1-continued tert-Butylamine (NH₃: C₄H₈ = 1.5)

tert-Butylamine yield [% by weight]

| Cat. | Temperature [° C.] | WHSV 0.38 [g/g·h] | WHSV 0.75 [g/g·h] | WHSV 1.5 [g/g·h] | WHSV 3 [g/g·h] | Density [kg/l] |
|---|---|---|---|---|---|---|
| B | 300 | | | | 12.73 | 0.56 |
| C | 270 | | 21.45 | 19.13 | 16.18 | 0.56 |
| E | 270 | | 21.00 | 19.89 | 16.78 | 0.45 |

We claim:

1. A process for preparing amines of the general formula I

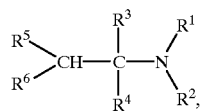
(I)

where $R^1, R^2, R^3, R^4, R^5, R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkyl-cycloalkyl, $C_4$–$C_{20}$-cycloalkyl-alkyl, aryl, $C_7$–$C_{20}$-alkylaryl or $C_7$–$C_{20}$-aralkyl, $R^1$ and $R^2$ are together a saturated or unsaturated divalent $C_3$–$C_9$-alkylene chain and $R^3$ or $R^5$ are $C_{21}$–$C_{200}$-alkyl, $C_{21}$–$C_{200}$-alkenyl or together a divalent $C_2$–$C_{12}$-alkylene chain, by reacting olefins of the general formula II

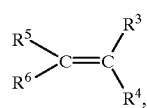
(II)

where $R^3$, $R^4$, $R^5$ and $R^6$ are as defined above, with ammonia or primary or secondary amines of the general formula III

(III)

where $R^1$ and $R^2$ are as defined above, at from 200 to 350° C. and pressures of from 100 to 300 bar in the presence of a heterogeneous catalyst, wherein the heterogeneous catalyst used is a zeolite having an NES structure.

2. A process for preparing amines I as claimed in claim 1, wherein the amine I formed is separated off and the unreacted starting materials II and III are recirculated.

3. A process for preparing amines as claimed in claim 1, wherein the olefin II used is isobutene, diisobutene, cyclopentene, cyclohexene or polyisobutene.

4. A process for preparing amines as claimed in claim 1, wherein the heterogeneous catalyst used is a zeolite having an NES structure in the H form.

5. A process for preparing amines as claimed in claim 1, wherein the heterogeneous catalyst used is a zeolite having an NES structure which has been treated with an acid, in particular one selected from the group consisting of hydrochloric acid, hydrofluoric acid, sulfuric acid, phosphoric acid, oxalic acid and mixtures thereof.

6. A process for preparing amines as claimed in claim 1, wherein the heterogeneous catalyst used is a zeolite having an NES structure which is doped with one or more transition metals.

7. A process for preparing amines as claimed in claim 1, wherein the heterogeneous catalyst used is a zeolite having an NES structure which is doped with one or more elements of the rare earths.

8. A process for preparing amines as claimed in claim 1, wherein the heterogeneous catalyst used is a zeolite having an NES structure in the ammonium form.

9. A process for preparing amines as claimed in claim 1, wherein the heterogeneous catalyst used is a zeolite having an NES structure which is doped with one or more elements selected from the group consisting of the alkali metals, alkaline earth metals and earth metals.

10. A process for preparing amines as claimed in claim 1, wherein the heterogeneous catalyst used is a zeolite having an NES structure which has been shaped together with a binder and calcined at from 200 to 600° C.

11. A process for preparing amines as claimed in claim 1, wherein the heterogeneous catalyst used is a dealuminated or deborated zeolite having an NES structure.

12. A process for preparing amines as claimed in claim 1, wherein the heterogeneous catalyst selected from the group consisting of zeolites having an NES structure is an NU-87 zeolite.

* * * * *